US012744129B2

(12) United States Patent
Huang et al.

(10) Patent No.: US 12,744,129 B2
(45) Date of Patent: Sep. 22, 2026

(54) METHOD FOR CONSTRUCTING VARIATION LITERATURE INTERPRETATION KNOWLEDGE BASE, AND INTERPRETATION METHOD AND ELECTRONIC DEVICE

(71) Applicant: BGI GENOMICS CO., LTD., Shenzhen (CN)

(72) Inventors: Daoling Huang, Shenzhen (CN); Quanlei Zeng, Shenzhen (CN); Yun Xiong, Shenzhen (CN); Shuixia Liu, Shenzhen (CN); Yuying Yuan, Shenzhen (CN); Ning Li, Shenzhen (CN)

(73) Assignee: BGI GENOMICS CO., LTD., Shenzhen (CN)

( * ) Notice: Subject to any disclaimer, the term of this patent is extended or adjusted under 35 U.S.C. 154(b) by 493 days.

(21) Appl. No.: 18/474,426

(22) Filed: Sep. 26, 2023

(65) Prior Publication Data

US 2024/0013931 A1 Jan. 11, 2024

Related U.S. Application Data

(63) Continuation of application No. PCT/CN2021/083203, filed on Mar. 26, 2021.

(51) Int. Cl.
*G06N 20/00* (2019.01)
*G06N 5/022* (2023.01)
*G16H 70/60* (2018.01)

(52) U.S. Cl.
CPC ............. *G16H 70/60* (2018.01); *G06N 5/022* (2013.01); *G06N 20/00* (2019.01)

(58) Field of Classification Search
CPC ......... G16H 70/60; G06N 20/00; G06N 5/022
See application file for complete search history.

(56) References Cited

U.S. PATENT DOCUMENTS 11,561,987 B1 * 1/2023 Sager .................... G06F 16/248
2020/0034719 A1 * 1/2020 Zhang .................... G16H 10/60
(Continued)

FOREIGN PATENT DOCUMENTS

CN 106708959 A 5/2017
CN 107357924 A 11/2017
(Continued)

OTHER PUBLICATIONS

International Search Report and Written Opinion for PCT/CN2021/083203 filed Mar. 26, 2021.
(Continued)

*Primary Examiner* — Stephen T Gundry
(74) *Attorney, Agent, or Firm* — George R. McGuire; Bond, Schoeneck & King PLLC

(57) ABSTRACT

Provided are an NLP-based method for constructing a variant literature interpretation knowledge base, an interpretation method, and an electronic device. The method for constructing the variant literature interpretation knowledge base includes: obtaining disease-related literature; constructing, based on the disease-related literature, a database of entities associated with genes and variants; constructing a literature evidence knowledge graph for interpretation of variant literature; and performing evidence extraction on the literature evidence knowledge graph to obtain evidence corresponding to an entity, and constructing, based on the evidence and the database, the variant literature interpretation knowledge base. In this way, the literature evidences can be more comprehensive and systematic. Thus, during interpretation, evidence standard or evidence type result based on literature reading can be automatically returned upon inputting an entity name, thereby achieving the automation and intelligence for obtaining disease variant litera-
(Continued)

ture evidence, and the interpretation speed related to genes and variants is effectively improved.

15 Claims, 7 Drawing Sheets

(56) References Cited

U.S. PATENT DOCUMENTS

| | | | | |
|---|---|---|---|---|
| 2020/0185072 | A1* | 6/2020 | Suarez Saiz | G16H 50/70 |
| 2020/0218779 | A1* | 7/2020 | Stevens | G16H 50/70 |
| 2023/0007965 | A1* | 1/2023 | Chen | G16H 50/70 |
| 2023/0038256 | A1* | 2/2023 | Tal | G06F 16/951 |
| 2023/0039937 | A1* | 2/2023 | Wendell | G06F 16/9024 |
| 2023/0050513 | A1* | 2/2023 | Morganella | G16B 20/20 |
| 2023/0117881 | A1* | 4/2023 | Sztyler | G16B 50/10 706/15 |
| 2023/0245788 | A1* | 8/2023 | Colley | G16H 20/00 702/19 |
| 2023/0326609 | A1* | 10/2023 | Paik | G16H 50/70 705/2 |
| 2023/0343468 | A1* | 10/2023 | Shapiro | G06F 40/205 |
| 2023/0350931 | A1* | 11/2023 | Lewis | G06F 16/3338 |
| 2023/0351111 | A1* | 11/2023 | Fauqueur | G06F 16/367 |
| 2023/0352193 | A1* | 11/2023 | Crowther | G06F 16/353 |
| 2024/0006021 | A1* | 1/2024 | Colavin | G06N 20/00 |
| 2024/0119232 | A1* | 4/2024 | Galitsky | G06F 40/295 |
| 2024/0312581 | A1* | 9/2024 | Colley | G16H 20/10 |
| 2024/0386015 | A1* | 11/2024 | Crabtree | G06F 16/9024 |
| 2025/0028984 | A1* | 1/2025 | Dutkowski | G06N 5/04 |
| 2025/0125060 | A1* | 4/2025 | Marks | G06F 40/205 |
| 2025/0279214 | A1* | 9/2025 | Beaubier | G16H 15/00 |

FOREIGN PATENT DOCUMENTS

| | | | | |
|---|---|---|---|---|
| CN | 110825721 A | | 2/2020 | |
| CN | 107357924 B | * | 4/2020 | G06N 5/025 |
| CN | 111428036 A | | 7/2020 | |
| CN | 111554360 A | | 8/2020 | |
| CN | 112100394 A | | 12/2020 | |
| CN | 112199511 A | | 1/2021 | |
| CN | 112287114 A | | 1/2021 | |
| CN | 112347773 A | | 2/2021 | |
| CN | 112466463 A | | 3/2021 | |
| WO | 2015113578 A1 | | 8/2015 | |

OTHER PUBLICATIONS

EP Search Report, Application No. 21932249.2-1203, Dated Jan. 2, 2025., Entire document.

Li, Marilyn M., et al., “Standards and Guidelines for the Interpretation and Reporting of Sequence Variants in Cancer”, Research article published in The Journal of Molecular Diagnostics; vol. 19, No. 1; Dated Jan. 1, 2017, Entire document.

Zhao, Di , et al., “Incorporating representation learning and multihead attention to improve biomedical cross-sentence n-ary relation extraction”, Research article published in BMC Bioinformatics, Biomed Ltd, London, UK; vol. 21, No. 1; Dated Jul. 16, 2020, Entire document.

Translated CN Office Action; Application No. 202180088232.5; Dated Nov. 26, 2025, Entire document.

* cited by examiner

| Literature identification information | Gene standard terms | Variant standard terms | ACMG evidence criterion | Evidence word | Evidence word |
|---|---|---|---|---|---|
| 0001 | Gene 1 | p.* | PS1 | [word 1, word 2] | [sentence 1] |
| 0002 | Gene 2 | p.* | PM1 | [word 3, word 4] | [sentence 2, sentence 3] |
| 0003 | Gene 3 | c.* | PM1 | [phrase 1, word 5] | [sentence 4, sentence 5] |
| 0004 | Gene 4 | rs.* | PP5 | [phrase 2, phrase 3] | [sentence 6] |
| …… | …… | …… | …… | …… | …… |

FIG. 6

METHOD FOR CONSTRUCTING VARIATION LITERATURE INTERPRETATION KNOWLEDGE BASE, AND INTERPRETATION METHOD AND ELECTRONIC DEVICE

CROSS-REFERENCE TO RELATED APPLICATIONS

This application is a continuation of International Application No. PCT/CN2021/083203, filed on Mar. 26, 2021, the disclosure of which is hereby incorporated by reference in its entirety.

FIELD

The present application relates to the field of biological information technology, and in particular, to an NLP-based method for constructing a variant literature interpretation knowledge base, and an interpretation method and an electronic device.

BACKGROUND

The rapid development of deoxyribonucleic acid (DNA) sequencing technology has generated enormous genomic data and has also resulted in a revolution of the diagnostic methods of genetic diseases, initiating the chapter of precise medicine. Combined with gene detection results and clinical interpretation guidelines formulated by various authorities, it has become a consensus to interpret clinically significant genes and variants with the guidance of evidence-based medicine. For example, the American College of Medical Genetics and Genomics (ACMG) has developed criteria and guidelines for the classification of genes and variants. Variant interpretation guidelines for tumor somatic cells have jointly developed by the Association for Molecular Pathology, American Society of Clinical Oncology, and College of American Pathologists. Computational and query-based software based on the various database compiled by the existing experts successively emerged, enabling automated or semi-automated interpretation of part of genes and variants. However, the variants included in the database are very limited. When the clinical laboratories issue clinical reports on the detected variants, they still mainly rely on the manual interpretation by professionals based on the variant interpretation guidelines. To interpretate a variant, the interpreter takes the variant and the corresponding gene as keywords to search relevant literature, and through reading the literature, analyzes and determines that the variant in the literature meets a certain criterion recommended by guidelines. Therefore, it is still a critical step in variant interpretation to obtain valuable interpretation information through manual reading of literature.

Obtaining variant literature evidence by manual reading has the following drawbacks. Firstly, the manual reading of literature is time-consuming and labor-intensive, and the results are very limited, making it a rate-determining step for variant interpretation. Secondly, manual reading of literature has high professional barriers because interpreters are required to have sufficient knowledge in variant interpretation. Furthermore, not only literature is in a huge number and rather scattered, but also there are various synonyms or aliases for an entity to be interpreted, such as gene, variant, drug, disease, and phenotype, etc. The interpreter often manually inputs one or several of the common synonyms or aliases as search keywords, leading to limited related literature. Therefore, it is difficult to obtain the evidence of variant literature quickly and comprehensively through manual reading. Accordingly, it has become an important bottleneck to improve the efficiency of interpretation.

SUMMARY

The present disclosure is intended to solve at least one of the technical problems in the related art to some extent. For this purpose, a first object of the present disclosure is to provide a method for constructing a Natural Language Processing (NLP)-based variant literature interpretation knowledge base, which enables the automation and intelligence of obtaining variant literature evidence and can effectively improve the interpretation speed associated with genes and variants. The literature evidences are more comprehensive, thereby advantageously improving the quality and efficiency of interpretation of gene detection report.

A second object of the present disclosure is to provide an NLP-based variant literature interpretation method.

A third object of the present disclosure is to provide an electronic device.

In order to achieve the above objects, in a first aspect of embodiments of the present disclosure, an NLP-based method for constructing a variant literature interpretation knowledge base is provided. The method includes: obtaining disease-related literature; constructing, based on the disease-related literature, a database of entities associated with genes and variants; constructing a literature evidence knowledge graph for variant interpretation; and performing evidence extraction on the literature evidence knowledge graph to obtain evidence corresponding to an entity, and constructing, based on the evidence and the database, the variant literature interpretation knowledge base.

In the NLP-based method for constructing the variant literature interpretation knowledge base according to the embodiments of the present disclosure, the disease-related literature is obtained; then a database of entities associated with gene and variants is constructed based on the disease-related literature; then a literature evidence knowledge graph for variant interpretation can be constructed; and evidence extraction is performed on the literature evidence knowledge graph to obtain evidence corresponding to an entity, and the variant literature interpretation knowledge base can be constructed based on the evidence and the database. In this regard, the present disclosure provides a method for obtaining disease literature evidence by machine-assisted automatic literature reading based on NLP and knowledge graph technology. Through the method for constructing the variant literature interpretation knowledge base, the literature evidence can be more comprehensive and systematic. Thus, during interpretation, when any entity name related to genes and variants is input, the result of variant evidence based on literature reading can be automatically returned to, thereby achieving the automation and intelligence for obtaining variant literature evidence of a disease, and the interpretation speed related to genes and variants can be effectively improved. The literature query result can be returned within seconds, which greatly improves the efficiency of literature search, and is further conducive to improving the quality and efficiency of interpretation of gene detection reports.

According to an embodiment of the present disclosure, said constructing, based on the disease-related literature, the database of entities associated with genes and variants includes: constructing an entity extraction model using certain literature of the disease-related literature; performing, through the entity extraction model, entity extraction on the remaining literature in the disease-related literature to obtain entity names; constructing an entity alignment model; performing, through the entity alignment model, entity alignment on the entity name to obtain an entity standard term corresponding to the entity name; and constructing, based on the entity name and the entity standard term corresponding to the entity name, the database of entities associated with genes and variants.

According to an embodiment of the present disclosure, said constructing the entity extraction model using some literature of the disease-related literature includes: performing entity annotating on certain literature; adding a position and an entity classification tag to each word in the entity-annotated literature to obtain an entity tag sequence; constructing a pre-training model of the entity extraction model; and adjusting, by using the entity tag sequence, the pre-training model to obtain the entity extraction model.

According to an embodiment of the present disclosure, said constructing the pre-training model of the entity extraction model includes: obtaining pre-training corpus, wherein the pre-training corpus includes relevant literature in the biomedical field; encoding each word in the pre-training corpus to obtain a word embedding vector, a segment embedding vector, and a position embedding vector; pre-training, using a back-propagation algorithm, a self-attention mechanism-based NLP model by taking the sum of the word embedding vector, the segment embedding vector, and the position embedding vector as an input and taking a random masking part of a word vector as a tag, to obtain the pre-training model.

According to an embodiment of the present disclosure, said constructing the pre-training model of the entity extraction model further includes: training the pre-training model by taking a cross entropy of a predicted value and the tag as a loss function, and finishing the training of the pre-training model until a loss value output by the loss function satisfies a pre-set condition.

According to an embodiment of the present disclosure, said training, by using the entity tag sequence, the pre-training model to obtain the entity extraction model includes: constructing, based on the pre-training model, a fine-tuning model of the entity extraction model; and training, using the back-propagation algorithm, the fine-tuning model to obtain the entity extraction model by taking a model weight obtained when training the pre-training model as an initial weight of an entity extraction task, taking a word embedding vector corresponding to each word in the entity-annotated literature as an input, and taking the position and the entity classification tag corresponding to each word as an output.

According to an embodiment of the present disclosure, the method further includes: training the fine-tuning model by taking the cross entropy of the predicted value and the tag as the loss function, and finishing the training of the fine-tuning model until the loss value output by the loss function satisfies the pre-set condition.

According to an embodiment of the present disclosure, the method further includes, subsequent to said performing, through the entity extraction model, the entity extraction on the remaining literature in the disease-related literature to obtain the entity name: matching the remaining literature with a pre-set entity dictionary and/or a pre-set entity writing pattern to supplement an entity name unrecognized by the entity extraction model.

According to an embodiment of the present disclosure, said constructing the entity alignment model includes: obtaining an entity standard term and the other entity names corresponding to the entity standard term, and constructing an entity alignment dictionary based on the entity standard term and the other entity names; and/or obtaining the entity standard term, and constructing an entity-aligned regular expression based on the entity standard term.

According to an embodiment of the present disclosure, the regular expression includes one or more of the following expressions: c. {any length number of length≥1 and the number of symbols≥0} {any length letter of length≥1}>{any length letter of length≥1 and the number of symbols≥0}; p. {any length letter of length≥1 and the number of symbols≥0} {any length number of length≥1} {any length letter of length≥1 and the number of symbols≥0}; rs{any length number of length≥1}; chr{any length letter of length≥1}–{any length number of length≥1}–{any length letter of length≥1 and the number of symbols≥0}–{any length letter of length≥1 and the number of symbols≥0}; n. {any length number of length≥1 and the number of symbols≥0} {any length letter of length≥1}>{any length letter of length≥1 and the number of symbols≥0}; IVS. {any length number of length≥1 and the number of symbols≥0} {any length letter of length≥1}>{any length letter of length≥1 and the number of symbols≥0}; {any length letter of length≥1} {any length number of length≥1} {any length letter of length≥1}.

According to an embodiment of the present disclosure, said performing, through the entity alignment model, the entity alignment on the entity name to obtain the entity standard term corresponding to the entity name includes: performing exact matching and fuzzy matching on the entity name and the entity alignment dictionary to obtain the entity standard term corresponding to the entity name; and/or performing exact matching and rule matching on the entity name and the regular expression to obtain the entity standard term corresponding to the entity name.

According to an embodiment of the present disclosure, the database of entities associated with genes and variants includes: {entity names: entity standard term} dictionary, (literature identification information, entity standard term) data list, and (literature identification information, entity name) data list.

According to an embodiment of the present disclosure, said constructing a literature evidence knowledge graph for variant interpretation includes: deriving one or more judgement rules for each evidence criterion or evidence type in variant interpretation guidelines; presenting each judgment rule in a form of a triplet, wherein the triplet is (entity, relationship between entity and evidence criterion or evidence type, evidence criterion or evidence type); and constructing the literature evidence knowledge graph by taking the entity and the evidence criterion or evidence type as a node and taking a relationship between the entity and the evidence criterion or evidence type as an edge.

According to an embodiment of the present disclosure, said performing the evidence extraction on the literature evidence knowledge graph to obtain the evidence corresponding to the entities, and constructing, based on the evidence and the database, the variant literature interpretation knowledge base includes: extracting, from an article corresponding to the database of the entities associated with the genes and variants, a sentence containing the node or the meaning of the node and upper and lower sentences of the sentence, and generating evidence sentence set corresponding to the node; extracting evidence words from the evidence sentence set; generating, based on the evidence sentence set and the evidence words, entity standard terms, evidence criteria or evidence types, evidence sentences, and evidence words corresponding to the literature; constructing the variant literature interpretation knowledge base based on the literature identification information and the entity standard terms, evidence criteria or evidence types, evidence sentences, and evidence words corresponding to the literature.

According to an embodiment of the present disclosure, the entity includes one or more of a gene, a variant, a drug, a disease, and a phenotype.

In order to achieve the above objects, in a second aspect embodiment of the present disclosure, an NLP-based variant literature interpretation method is provided. The method includes: obtaining an entity name to be interpreted; and inputting the entity name into a variant literature interpretation knowledge base to obtain an evidence criterion or evidence type, an evidence sentence, and an evidence word corresponding to the entity name, wherein the variant literature interpretation knowledge base is constructed with the above-mentioned NLP-based method for constructing a variant literature interpretation knowledge base.

In the NLP-based variant literature interpretation method according to the embodiments of the present disclosure, an entity name to be interpreted is obtained; the entity name is input into a variant literature interpretation knowledge base to obtain an evidence criterion or evidence type, an evidence sentence, and an evidence word corresponding to the entity name, in which the variant literature interpretation knowledge base is constructed with the method for constructing the variant literature interpretation knowledge base as described above. Thus, the corresponding evidence criterion or evidence type, evidence sentence, and evidence word can be automatically obtained by inputting the entity name. In this way, the automation and intelligence of obtaining disease variant literature evidence can be achieved, and the interpretation speed can also be effectively improved. Accordingly, and the literature evidence is more comprehensive, which is conducive to improving the quality and efficiency of interpretation of gene detection report.

In order to achieve the above object, in a third aspect embodiment of the present disclosure, an electronic device in provided. The electronic device includes a memory, a processor, and a variant literature interpretation program stored in the memory and executable on the processor. The processor, when executing the variant literature interpretation program, implements the above-mentioned NLP-based variant literature interpretation method.

In the electronic device according to the embodiments of the present disclosure, the above-mentioned NLP-based variant literature interpretation method is implemented when the variant literature interpretation program is executed by the processor. In this way, the corresponding evidence criterion or evidence type, evidence sentence, and evidence word can be automatically obtained by inputting the entity name, thereby realizing the automation and intelligence of obtaining disease variant literature evidence and effectively improving the interpretation speed. Accordingly, literature evidence is more comprehensive, which is conducive to improving the quality and efficiency of interpretation of gene detection report.

Additional aspects and advantages of the present disclosure will be set forth in part in the description which follows and, in part, will be obvious from the description, or may be learned by practice of the present disclosure.

BRIEF DESCRIPTION OF THE DRAWINGS

FIG. 6 is a schematic diagram of a variant literature interpretation knowledge base interface according to an embodiment of the present disclosure;

DETAILED DESCRIPTION

Figure 1:
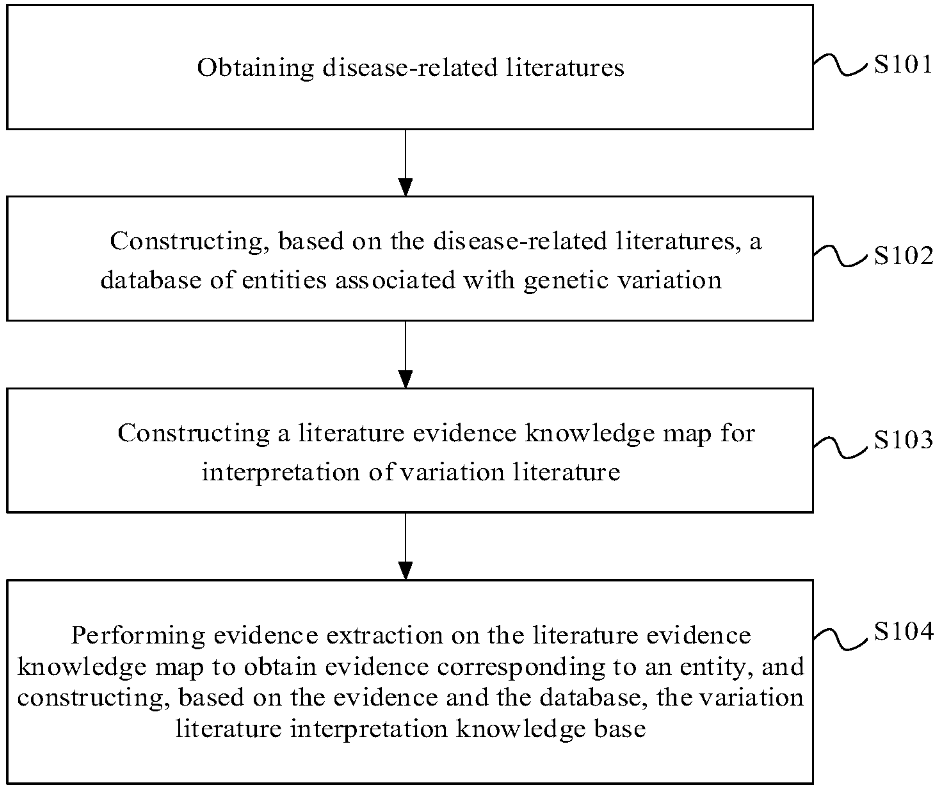
FIG. 1 is a flowchart of an NLP-based method for constructing a variant literature interpretation knowledge base according to an embodiment of the present disclosure.

The embodiments of the present disclosure are described in detail below. Examples of the embodiments of the present disclosure are illustrated in the accompanying drawings. The same or similar reference numerals represent the same or similar elements or the elements having the same or similarly functions throughout the drawings. The embodiments described below with reference to the drawings are exemplary and are intended to be illustrative rather than limiting the present disclosure.

An NLP-based method for constructing a variant literature interpretation knowledge base, and an interpretation method and an electronic device provided by the embodiments of the present disclosure are described below with reference to the accompanying drawings.

NLP is a field of computer science, artificial intelligence and computational linguistics concerned with interactions between computers and human languages. Due to the ambiguity of natural language texts, it is particularly important to learn words, express and extract information and relationship effectively. Over the past few decades, NLP has undergone a dramatic evolution from fundamental rules, statistics, to the current widespread use of deep learning techniques. In recent years, the in-depth learning NLP technology, which is represented by the Transformer framework proposed by Google in 2017 and based on a self-attention mechanism, has shined in fields such as machine translation, sentiment analysis, information extraction and automatic question answering. In general, this technology achieves supervised machine learning based on specific tasks by self-supervised learning based on massive corpus, learning pre-trained feature representations for text, and using these pre-trained feature representations as starting points for feature representation. A knowledge graph, as a human-interpretable and machine-friendly knowledge representation, is characteristic by its own semantics and logic rules, which is very important for knowledge reasoning.

Therefore, the present disclosure provides a method for constructing a variant literature interpretation knowledge base based on NLP and knowledge graph technology. In this method, entities associated with genes and variants in the literature are extracted and aligned to standard terms, to accurately and comprehensively screen the literature associated with the entity name to be interpreted; then, based on the judgment rule of the evidence criterion or evidence type used for literature interpretation in the variant interpretation guidelines, the literature evidence knowledge graph is constructed to obtain the corresponding evidence criterion or evidence type, evidence sentence and evidence word of the entity name to be interpreted. The judgment rule obtained by querying the knowledge graph with the entity name to be interpreted and the corresponding evidence-related sentences extracted from the literature can be provided as the literature evidence for the machine automatic literature reading.

It should be noted that, since the entity associated with genes and variants may include one or more of gene, variant, drug, disease, and phenotype entities, for ease of explanation, the present disclosure will be explained in the following embodiments using gene entities and variant entities. However, it can be understood that the present disclosure is not limited thereto.

FIG. 1 is a flowchart of an NLP-based method for constructing a variant literature interpretation knowledge base according to an embodiment of the present disclosure. As illustrated in FIG. 1, the NLP-based method for constructing the variant literature interpretation knowledge base may include the following steps.

Step S101: disease-related literature is obtained.

Disease-related literature is the data sources of the database to be built. The more relevant literature is obtained, the more comprehensive information can be obtained through searching. Therefore, the disease-related literature should be obtained as many as possible, to improve the comprehensiveness of literature evidences. Literature identification information can be assigned to the literature after the disease-related literature is obtained. The disease may be a genetic disease, which is not limited herein.

Step S102: a database of entities associated with genes and variants is constructed based on the disease-related literature.

Specifically, this step is to construct a database based on the disease-related literature obtained in step S101. The database is a database of entities associated with genes and variants, and the data may be in the form of a list and dictionary, and the data content may cover information such as literature identification information, gene name, variant name, gene standard term, and variant standard term. Specifically, by using NLP technology, an end-to-end model can be established by using entity name as the input and all the literature and related entities including the two as the output, to construct a database of entities associated with genes and variants. In this way, by inputting the corresponding entity name, all the related literature identification information can be returned. That is, by inputting any (gene name, variant name) pair, all the (gene standard term, variant standard term) pairs corresponding thereto can be obtained, and then all the equivalent (gene name, variant name) pairs can be obtained. Therefore, all relevant literature based on the meaning of the entity can be selected, thereby greatly broadening the scope of literature that can be searched by accurately matching individual (gene name, variant name) pairs, which is conducive to providing more comprehensive literature interpretation information for the variants.

In an embodiment, based on the disease-related literature, said constructing, based on the disease-related literature, the database of entities associated with genes and variants includes: constructing an entity extraction model using certain literature of the disease-related literature; performing, through the entity extraction model, entity extraction on the remaining literature in the disease-related literature to obtain an entity name; constructing an entity alignment model; performing, through the entity alignment model, entity alignment on the entity name to obtain an entity standard term corresponding to the entity name; and constructing, based on the entity name and the corresponding entity standard term, the database of entities associated with genes and variants.

That is, the construction of the above-mentioned end-to-end model includes construction of an entity extraction model and an entity alignment model. In the construction process, certain articles are first selected from the obtained literature to construct the entity extraction model, and then the entity extraction model is implemented on remaining literature, and the gene names and variant names obtained are aligned based on gene standard terms and variant standard terms, respectively, and then stored in a database. In addition, after the alignment of the gene names and variant names to be interpreted, an article query is conducted. In this way, various descriptions (e.g., synonyms) of the gene and the variant to be interpreted can be used as query objects, to identify more relevant literature, thereby providing comprehensive literature evidences.

In an embodiment, said constructing the entity extraction model using some literature of the disease-related literature includes: performing entity annotating on certain literature; adding a position and an entity classification tag to each word in the entity-annotated literature to obtain an entity tag sequence; constructing a pre-training model of the entity extraction model; and adjusting, by using the entity tag sequence, the pre-training model to obtain the entity extraction model.

Figure 2:
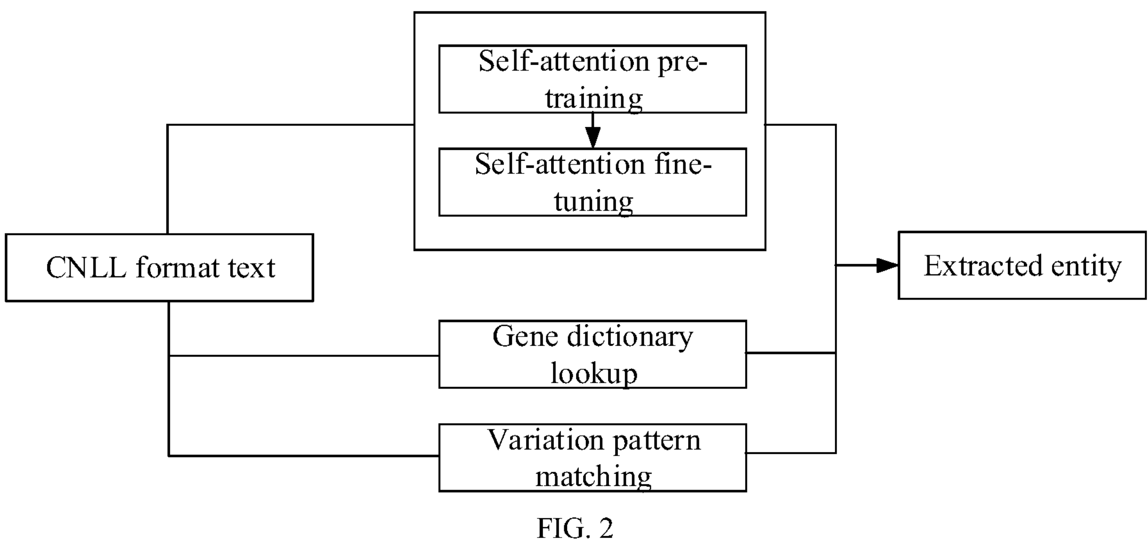
FIG. 2 is a schematic diagram of constructing an entity extraction model according to an embodiment of the present disclosure.

Specifically, the entity extraction model can refer to FIG. 2. The entity extraction model can be implemented through self-attention pre-training, self-attention fine-tuning, gene dictionary lookup, and variant pattern matching in cnll format text. The core thereof is an NLP model based on a self-attention mechanism, in which the input is an article and the output is an entity name extracted from the literature through transfer learning.

Specifically, in constructing an entity extraction model using partial literature in disease-related literature, gene entities and variant entities are annotated on the partial literature to obtain annotated corpus, and a position and an entity classification tag are added to the entity-annotated corpus to obtain an entity tag sequence. The position information can be expressed in the form of "BIO" (Begin, Inside, Other) or "BIES" (Begin, Inside, End, Single), and the entity classification tag can be gene or variant. Then, the pre-training model of the entity extraction model is constructed, and the pre-training model is adjusted using the entity tag sequence. The adjustment can be finetuning so as to improve the entity extraction model.

In an embodiment, said constructing the pre-training model of the entity extraction model includes: obtaining pre-training corpus, wherein the pre-training corpus includes relevant literature in the biomedical field; encoding each word in the pre-training corpus to obtain a word embedding vector, a segment embedding vector, and a position embedding vector; pre-training, using a back-propagation algorithm, a self-attention mechanism-based NLP model by taking the sum of the word embedding vector, the segment embedding vector, and the position embedding vector as an input and taking a random masking part of a word vector as a tag, to obtain the pre-training model.

In an embodiment, said constructing the pre-training model of the entity extraction model further includes: training the pre-training model by taking a cross entropy of a predicted value and the tag as a loss function, and not finishing the training of the pre-training model until a loss value output by the loss function satisfies a pre-set condition.

Figure 3:
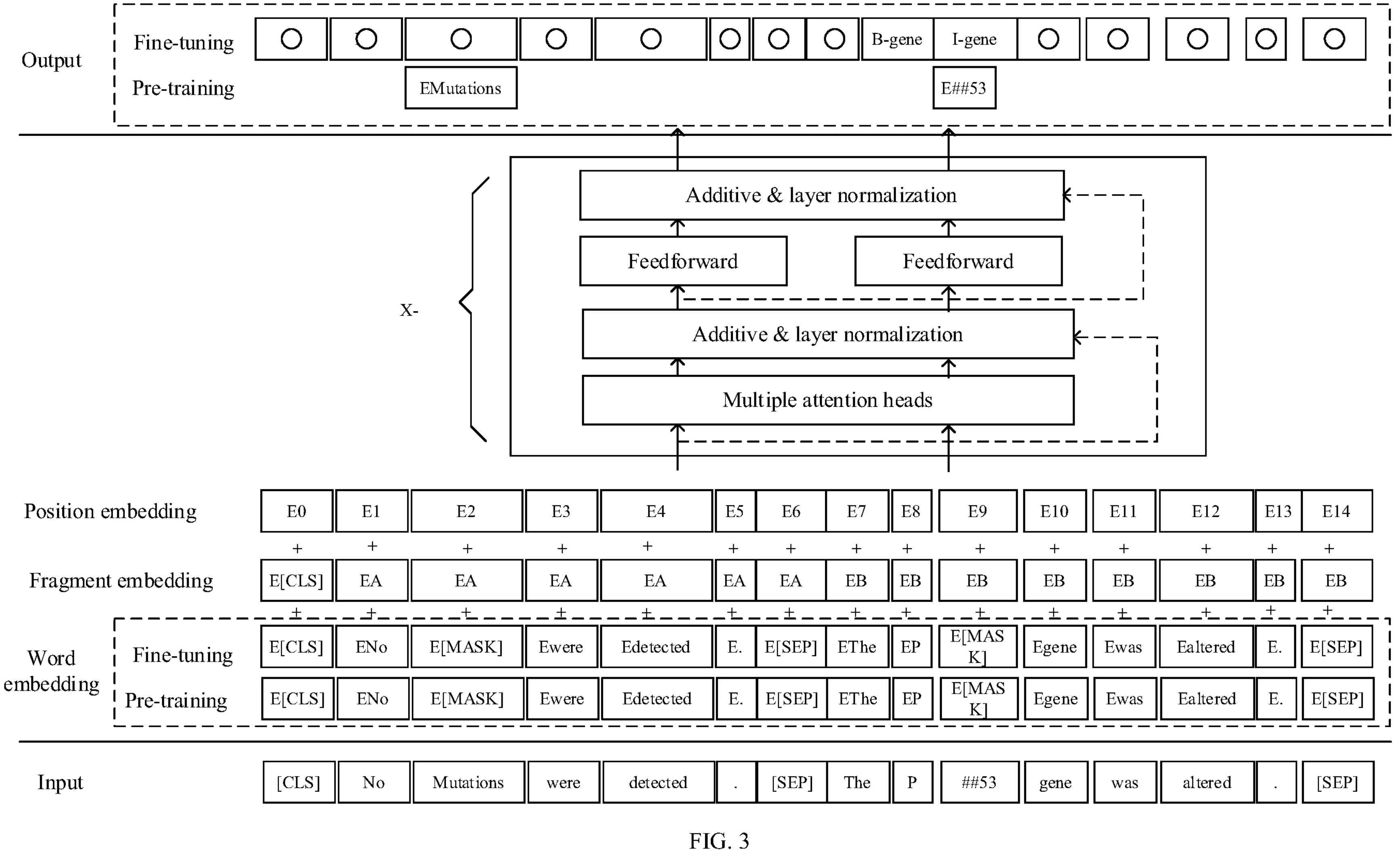
FIG. 3 is a schematic diagram of an entity extraction model based on a self-attention mechanism according to an embodiment of the present disclosure.

In implementation, the pre-training model of literature in the biomedical field can be constructed first. FIG. 3 is a schematic diagram of an entity extraction model based on a self-attention mechanism according to an embodiment of the present disclosure. As illustrated in FIG. 3, a pre-training feature extractor is composed of encoders composed of stacked converters, and each encoder can have a plurality of attention heads. Different encoders and attention heads can extract different levels of semantic information of a corpus represented by features. During the training of the pre-training model, a single sentence prediction or a next sentence prediction (NSP) can be selected. The sentence in the single sentence prediction can be represented as: [CLS] sentence; in the next sentence prediction, the sentence pairs are represented as follows: [CLS] sentence 1 [SEP] sentence 2 [SEP]. In the pre-training model training, the final hidden state marked by inputting [CLS] is used as a classifier to correspondingly predict whether the feature information of a single sentence or two sentences in a sentence pair appears sequentially in the corpus. Each word in the training data sentence is mapped to the sum of the corresponding word embedding vector, segment embedding vector, and position embedding vector. Some sub-word vectors are randomly masked as tags, which are pre-trained by the back-propagation algorithm. The coding vector corresponding to each word obtained from the attention layer is a weight for calculating the relevance of the word to all the words, in accordance with the following equation:

$$\text{Attention}(Q, K, V) = \sum_{i=1}^{L} \frac{\exp(Q^T K_i)}{\sum_j^L \exp(Q^T K_j)} V_i$$

where Q, K, and V represent Query, Key, and Value, respectively, and L represents the length of the entire input.

Then, the pre-training model based on the entity extraction of the self-attention mechanism is trained and optimized. Specifically, the model can be trained by taking the cross entropy of the predicted value and the tag as a loss function. In a specific example, the model can be optimized by adjusting hyper-parameters such as the number of network layers, inputting the sentence length, the batch size, the epochs, etc.

In an embodiment, said training, by using the entity tag sequence, the pre-training model to obtain the entity extraction model includes: constructing, based on the pre-training model, a fine-tuning model of the entity extraction model; and training, using the back-propagation algorithm, the fine-tuning model to obtain the entity extraction model by taking model weights obtained from the pre-training model as initial weights of an entity extraction task, taking a word embedding vector corresponding to each word in the entity-annotated literature as an input, and taking the position and the entity classification tag corresponding to each word as an output.

In an embodiment, the fine-tuning model is trained by taking the cross entropy of the predicted value and the tag as the loss function, until the loss value output by the loss function satisfies the pre-set condition, and then the training of the fine-tuning model finishes.

Specifically, a fine-tuning model based on the task of entity extraction can be constructed first. As illustrated in FIG. 3, the model weights obtained by the pre-training model is taken as initial weights of the entity extraction task, the input is a word embedding vector corresponding to each word in a sentence, and the output is a position and an entity classification tag corresponding to each word, such as "B-gene", "I-gene", "B-variant", "I-variant", "O", etc. The fine-tuning model can be adjusted by using the back-propagation algorithm based on specific tasks, to obtain entity classification tag prediction. Then, the fine-tuning model based on the entity extraction of the self-attention mechanism is trained and optimized. In a specific example, the model can be trained by taking the cross entropy of the predicted value and the tag as a loss function. In a specific example, the model can be optimized by adjusting hyper-parameters such as the number of network layers, inputting the sentence length, the batch size, the epochs, etc.

In an embodiment, the method further includes, subsequent to said performing, the entity extraction model on the remaining literature in the disease-related literature to obtain the entity name, matching the remaining literature with a pre-set entity dictionary and/or a pre-set entity writing pattern to supplement entity names unrecognized by the entity extraction model.

Specifically, the gene name dictionary and the writing patterns of variant names can be obtained as comprehensively as possible. The gene name dictionary can be obtained from public data sources, such as gene-related databases, including, but not limited to, HUGO Gene Nomenclature Committee (HGNC) and National Center for Biotechnology Information (NCBI) databases. After the training of the fine-tuning model is finished, the optimized entity extraction model can be implemented to the literature to be tested, such as matching the text with the gene name dictionary, and performing pattern matching on the variant entities, to supplement the entities not recognized by the entity extraction model.

In an embodiment, said constructing the entity alignment model includes obtaining an entity standard term and as many as aliases, and constructing an entity alignment dictionary based on the entity standard term and aliases; and/or obtaining the entity standard term, and constructing an entity-aligned regular expression based on the entity standard term.

Specifically, in one aspect, in the process of gene alignment, in order to make the literature evidence more comprehensive, the entity alignment model should be constructed by obtaining as many gene standard terms as possible, which can be selected from public databases, including but not limited to HGNC and NCBI. Correspondingly, the constructed gene alignment dictionary is associated with the obtained gene standard terms and as many aliases, pseudonyms, etc. as possible. For instance, there are a series of aliases for the gene named APOBEC1 complementation factor (such as ACF, ASP, ACF64, ACF65, and APOBEC1CF, etc.). When constructing the gene alignment dictionary, A1CF can be selected as the standard term of gene, and all other aliases are the A1CF gene names.

On the other hand, in the process of variant alignment, the variant standard term can be determined according to the variant rules of the Human Genome Variant Society (HGVS). It should be noted that, unlike the gene name, the diversification of the variant name mainly lies in the diversification of the writing format of the variant, for example, c.1427A>G, 1427A>G, 1427AG, A1427G, c.DNA1427A>G, etc. are equivalent to c. 1427A>G. Therefore, it is preferable to construct the regular expression of variant alignment based on the standard terms of variants.

The regular expressions may include, but are not limited to, one or more of the following expressions: c. {any length number of length≥1 and the number of symbols≥0} {any length letter of length≥1}>{any length letter of length≥1 and the number of symbols≥0}; p. {any length letter of length≥1 and the number of symbols≥0} {any length number of length≥1} {any length letter of length≥1 and the number of symbols≥0}; rs{any length number of length≥1}; chr{any length letter of length≥1}–{any length number of length≥1}–{any length letter of length≥1 and the number of symbols≥0}–{any length letter of length≥1 and the number of symbols≥0}; n. {any length number of length≥1 and the number of symbols≥0} {any length letter of length≥1}>{any length letter of length≥1 and the number of symbols≥ 0}; IVS. {any length number of length≥1 and the number of symbols≥0} {any length letter of length≥1}>{any length letter of length≥1 and the number of symbols≥0}; {any length letter of length≥1} {any length number of length≥1} {any length letter of length≥1}.

In an embodiment, said performing, through the entity alignment model, the entity alignment on the entity name to obtain the entity standard term corresponding to the entity name includes performing exact matching and fuzzy matching on the entity name and the entity alignment dictionary to obtain the entity standard term corresponding to the entity name; and/or performing exact matching and rule matching on the entity name and the regular expression to obtain the entity standard term corresponding to the entity name.

Figure 4:
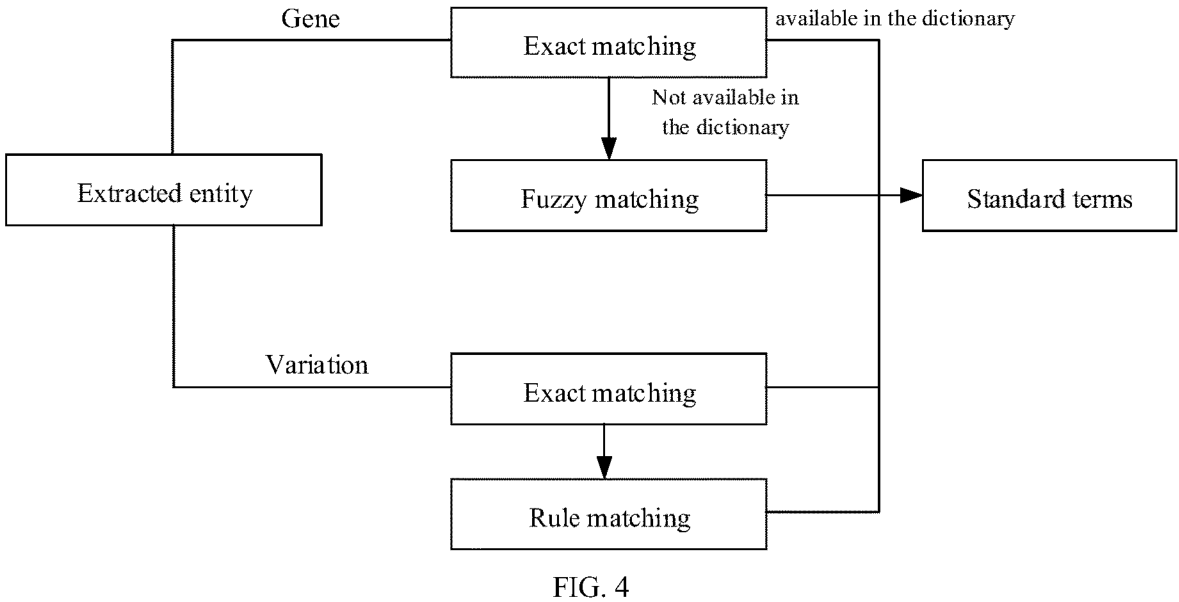
FIG. 4 is a schematic diagram of constructing an entity alignment model according to an embodiment of the present disclosure.

That is to say, as illustrated in FIG. 4, after the construction of the gene alignment dictionary is finished, all the gene names obtained by the entity extraction model are accurately matched with all the gene names in the above-mentioned gene alignment dictionary, and the successfully and accurately matched names (gene name, gene standard term) are saved. Then, the fuzzy matching is performed in cases when exact match does not work, and the gene names with the highest matching similarity (gene names, gene standard terms) are selected and saved. With regard to the variant alignment, all the variant names obtained from the entity extraction model are accurately matched with the regular expression pattern, and those successfully accurately matched names (variant names and variant standard terms) are saved; and then the variant names that are not successfully exact matched was rule matched with the regular expression pattern, and those that the rule matching was successful (variant names, variant standard terms) are saved.

Step S103: a literature evidence knowledge graph for variant interpretation is constructed.

Specifically, the knowledge graph, as a man-machine friendly knowledge representation, can visually highlight the logic rules and facilitate knowledge reasoning. The present disclosure can construct a literature evidence knowledge graph in combination with relevant contents of literature. Taking the construction of the ACMG literature evidence knowledge graph as an example, the concise and abstract evidence criteria of ACMG guidelines are embodied and enriched, which can realize knowledge reasoning of gene and variant and generate evidence levels automatically. It can be understood that, in the embodiments of the present disclosure, the ACMG variant interpretation guidelines are used as a reference for the construction of knowledge graphs and knowledge bases, but the present disclosure is not limited thereto, which can be readily understood and accepted by researchers in this field.

In an embodiment, said constructing a literature evidence knowledge graph for interpretation of variant literature includes obtaining a judgment rule of evidence criterion or evidence type used for literature interpretation in variant interpretation guidelines; presenting the judgment rule in a form of a triplet, wherein the triplet is (entity, relationship between entity and evidence criterion or evidence type, evidence criterion or evidence type); and constructing the literature evidence knowledge graph by taking the entity and the evidence criterion or evidence type as a node and taking a relationship between the entity and the evidence criterion or evidence type as an edge.

Figure 5:
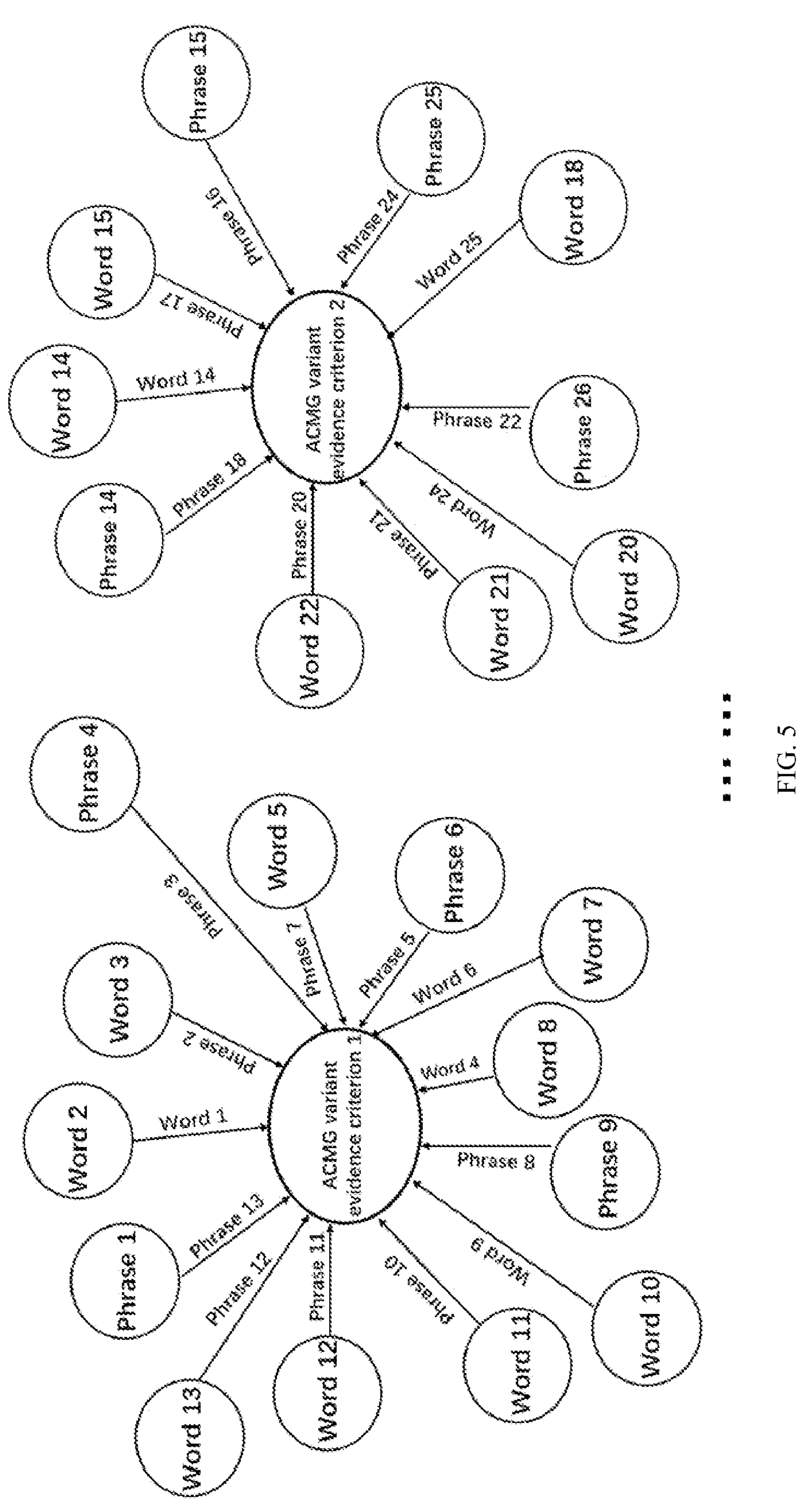
FIG. 5 is a schematic diagram of a literature evidence knowledge graph according to an embodiment of the present disclosure.

In the specific implementation, taking the ACMG variant interpretation guidelines as an example, the judgment rules of all the evidence criteria required for literature interpretation in the ACMG guidelines can be mined first and written in the form of triplet (entity, relationship between entity and evidence criterion or evidence type, evidence criterion or evidence type). As illustrated in FIG. 5, an entity and an evidence criterion or evidence type correspond to a node of an ACMG literature evidence knowledge graph, while the relationship between the entity node and the evidence criterion or evidence type corresponds to an edge of the above knowledge graph (where Word represents an entity standard term in the form of a word; Phrase represents an entity standard term in the form of a sentence; and ACMG variant evidence criterion represents ACMG literature evidence). Then the abstract ACMG evidence criterion corresponding to each node and edge of the knowledge graph is expanded the content of the knowledge graph. For example, an abstract description in the ACMG variant interpretation guidelines, "Pathogenic Variant", actually corresponds to multiple variants, and a mapping relationship between "Pathogenic Variant" and multiple variants can be constructed. Finally, based on the refined knowledge graph information, the knowledge graph of all the evidence criteria required in ACMG variant interpretation guidelines was constructed, which was used as the ACMG literature evidence criteria for genes and variants to be interpreted.

Step S104: evidence extraction is performed on the literature evidence knowledge graph to obtain evidence corresponding to an entity, and a variant literature interpretation knowledge base is constructed based on the evidence and the database.

In an embodiment, said performing the evidence extraction on the literature evidence knowledge graph to obtain the evidence corresponding to the entities such as a gene and a variant, and constructing, based on the evidence and the database, the variant literature interpretation knowledge base includes extracting, from an article corresponding to the database of the entities associated with the genes and variants, a sentence containing the node or the meaning of the node and upper and lower sentences of the sentence, and generating evidence sentence set corresponding to the node; extracting evidence words from the evidence sentence set; generating, based on the evidence sentence set and the evidence words, entity standard terms, evidence criteria or evidence types, evidence sentences, and evidence words corresponding to the literature; constructing the variant literature interpretation knowledge base based on the literature identification information and the entity standard terms, evidence criteria or evidence types, evidence sentences, and evidence words corresponding to the literature.

In the specific implementation, a sentence containing a node or nodes or the meanings of the node(s) in the literature evidence knowledge graph and the upper and lower three sentences of the sentence can be extracted from the literature corresponding to the database of entities associated with genes and variants. The node meanings and corresponding evidence sentence set can be saved, and the evidence sentence set can be saved in the form of an evidence sentence list. It should be noted that the node meaning herein refers to a word that has an equivalent meaning to an entity node in the literature evidence knowledge graph. From the saved node meaning and the corresponding evidence sentence set, the evidence words can be further extracted, and these evidence words represent the relationship between the entity nodes connected by the edge in the literature evidence knowledge graph and the evidence criterion or evidence type. That is, the words that have equivalent meanings to words representing relationships in the literature evidence knowledge graph are extracted. Then, based on the node meaning and the corresponding evidence sentence set, the evidence words generate the corresponding information of gene standard terms, variant standard terms, evidence criteria or evidence types and evidence words, and then, in combination with the literature identification information and evidence sentences, the variant literature interpretation knowledge base is finally generated, containing literature identification information, gene standard terms, variant standard terms, evidence criteria or evidence types, evidence words and evidence sentences. It should be noted that evidence words may include evidence words and evidence phrases. The variant literature interpretation knowledge base can be, but is not limited to, as illustrated in FIG. 6.

When interpreting, any pair (gene name, variant name) or a batch of pairs are input, i.e., the corresponding literature evidence criterion or evidence type can be obtained in an automatic literature reading knowledge base constructed based on NLP and knowledge graph technology. Such automatic literature reading knowledge base can be updated in real-time as the literature is updated, thereby providing the evidence criteria or evidence types related to the literature of variants efficiently, accurately, and comprehensively.

The NLP-based method for constructing the variant literature interpretation knowledge base provided in the present disclosure is further described below by means of a specific embodiment. As an example, the entities associated with genes and variants are genes and variants.

1. Obtaining 10000 disease-related literature such as genetic diseases, and assigning the disease-related literature with literature identification information (ID).
2. Based on the above 10000 literature, constructing a data list (literature identification information, gene standard terms, and variant standard terms), enabling all relevant literature identification information to be returned by inputting (gene name, variant name) in query. The specific steps are as follows:

2.1. Constructing an entity extraction model, which mainly includes two stages, i.e., construction and application, which are described in detail below.

2.1.1. Construction of Entity Extraction Model (1) A few (e.g., 500) articles were manually annotated and the entities included at least genes and variants.

Here, two annotated sentences in the article of DOI: 10.1007/s10048-011-0299-0 were taken as an example (where annotated entity names are indicated with{ }):

Sentence No.1:

New mutations in the ATM {gene} gene and clinical data of 25 AT patients.

Sentence No.2:

Analysis of patient derived mRNA by cDNA sequencing confirmed the pathogenic character of c.3285-2A>G {variant}, which results in an insertion of one nucleotide and a frame shift as the consequence (p.Leu1096IlefsX26){variant}.

(2) All gene names from public data sources (such as gene-related databases HGNC, NCBI, etc.) were obtained; variants are written in all possible patterns. In this example, the entity names were all more than 100,000 entries, and examples of the variant writing patterns were as follows:

```
Pattern No.1: "[cgrm]\.[0-9]+[ATCGatcgu]+\>[ATCGatcgu]+$"
Pattern No.2: "IVS[ATCGatcgu \/\>\?\(\)\[\]\;\:\*\_\-\þ 0-9]+$"
Pattern No.3: "[p]\.[CISQMNPKDTFAGHLRWVEYX \/\>\_\-\+0-9]+$"
Pattern No.4: "rs[0-9]+$"
......
```

(3) The annotated corpus (literature) in step (1) was processed into cnll format, i.e., adding a location and entity classification tag for each word in the text. Taking Sentence No. 1 in the above as an example, its cnll format is shown as follows:

```
New 0
mutation 0
in 0
the 0
ATM B-gene
gene 0
and 0
clinical 0
data 0
of 0
25 0
AT 0
patients 0
```

(4) Abstracts of a large number of articles in the biomedical field (e.g., 500,000 articles from PubMed databases) were obtained and used as a pre-training corpus for entity extraction models. Taking Sentence No. 1 in the above as an example, each word such as "New", "mutation", "in", . . . "patients" in the text was encoded into a word embedding vector, a segment embedding vector, and a position embedding vector, and the sum of these vectors was taken as an input vector, and part of the word vectors were randomly marked as a tag, to construct a pre-training model (see FIG. 3). The masked texts should be able to be predicted when the NLP model based on the self-attention mechanism was implemented on the whole text.

(5) A pre-training model of entity extraction based on a self-attention mechanism in step (4) was trained and optimized. The model was trained using the cross entropy of the predicted value and the tag as a loss function, adjusting the number of network layers such as 1 to 12 layers, inputting the sentence length such as [128, 256, 512], the batch size such as [8, 16, 32, 64], and the number of training rounds such as 5 to 10, etc.

(6) Based on the pre-training model framework, a fine-tuning model was constructed. The model weights obtained by the pre-training model are taken as initial weights of the entity extraction task, the input is a word embedding vector corresponding to each word in the literature, and the output is a position and an entity classification tag corresponding to each word, such as "B-gene", "I-gene", "B-variant", "I-variant", "O", etc. The model was learned through a back-propagation algorithm to obtain the tag prediction.

(7) A fine-tuning model of entity extraction based on a self-attention mechanism in (6) was trained and optimized. The fine-tuning model was trained using the cross entropy of the predicted value and the tag as a loss function. In this example, the number of network layers can be adjusted to, for example, 1 to 12 layers; the sentence length can be adjusted to, for example, [128, 256, 512], the batch size can be adjusted to, for example, [8, 16, 32, 64], and the number of training rounds can be adjusted to, for example, 5 to 10, etc. The F1-score (a measure of classification problems) for both genes and variants extracted by the fine-tuning model was above 92%.

2.1.2. Application of Entity Extraction Model (1) The remaining 9500 articles were predicted by the optimized entity extraction model.

(2) The obtained prediction was post-processed, for example, matching the text with the gene name dictionary which has been obtained during the construction, and performing pattern matching on the variant name to supplement entities which are not recognized by the entity extraction model.

2.2. Constructing an entity alignment model, mainly including gene alignment and variant alignment (see FIG. 4). The specific steps are as follows:

2.2.1. Gene Alignment (1) Gene abbreviation names commonly recognized by HGNC and NCBI were obtained from public databases as gene standard terms.

(2) An alignment dictionary corresponding to the gene standard terms and other names of the gene was constructed. For example: the "ATM" gene in Sentence No. 1 is a gene standard term, a gene alignment dictionary entry about "ATM" is constructed, and the entity expression thereof is:

{'ATM', 'TELO1', 'ATD', 'TEL1, telomere maintenance 1, homolog (*S. cerevisiae*)', 'ATDC', 'ATC', 'ATD', 'A-T mutated', 'ATM serine/threonine kinase', 'TEL1', 'ATA', 'serine-protein kinase ATM', 'ataxia telangiectasia mutated (includes complementation groups A, C and D)', 'ataxia telangiectasia mutated', 'ATDC', 'TEL1, telomere maintenance 1, homolog', 'TELO1', 'AT mutated', 'ATE', 'ATC', 'AT1'}

(3) All gene names obtained by the entity extraction model were accurately matched with gene standard terms in the gene alignment dictionary, and the matched (gene names, gene standard terms) are saved. Taking the gene named "ATM" extracted from Sentence No. 1 as an example, "ATM" was accurately matched with the gene alignment dictionary, and the matched result was ("ATM", "ATM"), and the result was saved.

(4) Through the above-mentioned step (3), if all the gene names extracted were successfully matched with the gene standard terms in the gene alignment dictionary, the step of gene fuzzy matching is skipped. Otherwise, the fuzzy matching was required to be performed, and the fuzzy matching can be string fuzzy matching, and the one with the highest matching similarity (gene name, gene standard term) was saved.

2.2.2. Variant Alignment (1) Standard writings of variant entities were determined and exact matching (e.g., regularized pattern matches) or rule matching were performed. Taking the variants "c. 3285-2A>G" and "p.Leu1096IlefsX26" in the above-mentioned Sentence No. 2 as an example, these two variants were converted into the following two writing formats respectively:

c. {any length number with length>=1, may contain symbol} {any length letter with length>=1} {any length letter with length>=1, may contain symbol};

p. {any length letter with length>=1, may contain symbol} {any length number with length>=1} {any length letter with length>=1, may contain symbol}.

Specifically, the variant "c. 3285-2A>G" starts with "c.", and the alignment format complies with the pattern of c. {any length number with length>=1, may contain symbol} {any length letter with length>=1}>{any length letter with length>=1, may contain symbol}. Thus, it could be aligned as "c. 3285-2A>G", and the matching results ("c. 3285-2A>G", "c. 3285-2A>G") were saved. The variant entity "p.Leu1096IlefsX26" starts with "p.", and the alignment format complies with the pattern of p. {any length letter with length>=1, may contain symbol} {any length number with length>=1} {any length letter with length>=1, may contain symbol}, and "X" was replaced with "*" based on the variant naming rule. Thus, it could be aligned as "p.Leu1096Ilefs*26", and the matching results ("p.Leu1096IlefsX26", "p.Leu1096Ilefs*26") were saved.

2.3. Construction of a database of genes and variants, the database of genes and variants including, but not limited to, the following 4 data storage units:

I{gene name: gene standard terms} dictionary;

II{variant name: variant standard terms} dictionary;

III (literature identification information, gene standard terms, and variant standard terms) data list; and IV (literature identification information, gene name, and variant name) data list.

Specifically, taking the gene name "ATM" in Sentence No. 1 , the variant name "c. 3285-2A>G" and "p.Leu1096IlefsX26" in Sentence No. 2 as examples, the construction of Table III was explained: assuming that the literature identification information of the article DOI: 10.1007/s10048-011-0299-0 is 1, "ATM" (gene name) corresponds to "ATM" (gene standard term), "c. 3285-2A>G" (variant name) corresponds to "c. 3285-2A>G" (variant standard term), and "p.Leu1096IlefsX26" (variant name) corresponds to "p.Leu1096Ilefs*26" (variant standard term), the item (1, "ATM", ["c. 3285-2A>G", "p.Leu1096Ilefs*26"]) in Table III can be obtained.

Therefore, any pair (gene name, variant name) can be input to correspond to all the pairs (gene standard term and variant standard term) corresponding thereto, and then correspond to all the equivalent pairs (gene name, variant name). Thus, all relevant literature based on entity meaning can be selected, which greatly widens the scope of literature that can be searched by accurately matching individual pairs (gene name, variant name), and which is conducive to providing more comprehensive literature reference information for the variants to be interpreted.

3. Construction of ACMG Literature Evidence Knowledge Graph 3.1. Taking the PS3 evidence criterion in the ACMG variant interpretation guidelines as an example, its judgment rule was obtained. The content of the PS3 evidence criterion is as follows:

PS3: Well-established in vitro or in vivo functional studies supportive of a damaging effect on the gene or gene product For the variant to be queried, the judgment rule for the PS3 evidence criterion can be written as: (Well-established in vitro or in vivo functional studies, supportive of a damaging effect on the gene or gene product, PS3).

3.2. The abstract terms in PS3 in step 3.1 can be specified to refine the knowledge graph for entity linking. For example, "Well-established in vitro or in vivo functional studies" in the PS3 evidence criterion can be expanded to a wide variety of functional testing approaches, including "cDNA sequencing" in Sentence No. 2, while "supportive of a damaging effect on the gene or gene product" can be expanded to a wide variety of "damaging" features, such as "pathogenic" and "insertion of one nucleotide and a frame shift" in Sentence No. 2. Therefore, Sentence No. 2 provides the following triplet of ACMG literature evidence knowledge graphs required to determine ("ATM", "c. 3285-2A>G") as the PS3 evidence criterion:

("all established in vitro or in vivo functional studies including cDNA sequencing", "all damaging effects on the gene or gene product including pathogenic/insertion of one nucleotide/frame shift", PS3)

4. Extracting Evidence Words and Evidence Sentences, and then Constructing a Variant Literature Interpretation Knowledge Base 4.1. As an example, ("ATM", "c. 3285-2A>G") in the extracted article DOI: 10.1007/s10048-011-0299-0 is from PS3 evidence sentence: firstly, by extracting the node "cDNA sequencing" connected to the node of PS3 evidence criterion in the ACMG literature evidence knowledge graph constructed in step 3.2, Sentence No. 2 and its upper and lower three sentences can be obtained, thereby generating evidence sentence set. The obtained evidence sentence set can be expressed in the format of {"cDNA sequencing": evidence sentence set} as follows:

{"cDNA sequencing": ("Analysis of patient derived mRNA by cDNA sequencing confirmed the pathogenic character of c.3285-2A>G, which results in an insertion of one nucleotide and a frame shift as the consequence (p.Leu1096IlefsX26).", "We found a previously described nonsense mutation, c.362T>A (pLeu362X), together with a new change, c.4110-9C>G, as the potential second disease causing mutation in a Russian patient.", "Further analysis of the latter alteration revealed that it activates a cryptic splice site resulting in an mRNA containing eight additional bases leading to a frame shift and thus confirming the transversion c.4110C>G as a pathogenic mutation.", "A further new splice site mutation, c.3285-2A>G, was found in patient 14587 in combination with a known protein truncating mutation on the other allele.", "This alteration was not detected in 294 alleles from unaffected controls.", "We found a not previously described deletion of 5 bp in exon 57 of the ATM gene, c.5260_5264delAAGAT, in a Turkish patient which can be predicted to lead to a frame shift and premature termination of protein translation (p.Lys1754AspfsX13).", "This mutation was accompanied by a missense mutation, c.6047A>G (p.Asp2016Gly), which was previously illustrated to be pathogenic due to a dramatically reduced ATM protein level in a patient homozygous for this mutation and with a protracted disease course.")}

4.2 From the data generated in step 4.1, the evidence words representing head node characteristics connecting the head node "cDNA sequencing" and tail node PS3 in the ACMG literature evidence knowledge graph can be further extracted, with the results of "pathogenic" and "insertion of one nucleotide frame shift", to generate the PS3 evidence criterion of "c. 3285-2A>G" corresponding to this article: {"c.3285-2A>G": [("cDNA sequencing", "pathogenic", PS3), ("cDNA sequencing", "insertion of one nucleotide", PS3), ("cDNA sequencing", "frame shift", PS3)]}.

Finally, the data (1, "ATM", "c.3285-2A>G", PS3, ["cDNA sequencing", "pathogenic", "insertion of one nucleotide", "frame shift"], ["Analysis of patient derived mRNA by cDNA sequencing confirmed the pathogenic character of c.3285-2A>G, which results in an insertion of one nucleotide and a frame shift as the consequence (p.Leu1096IlefsX26)."]), which was composed of literature identification information, gene standard terms, variant standard terms, ACMG evidence criterion, evidence words, and evidence sentences, was stored in the ACMG variant literature interpretation knowledge base, as is illustrated in FIG. 6.

When interpreting, inputting ("ATM", "c. 3285-2A>G") returned a series of results in the automatic reading literature knowledge base. The results include the knowledge of (1, "ATM", "c.3285-2A>G", ["cDNA sequencing", "pathogenic", "insertion of one nucleotide", "frame shift"], ["Analysis of patient derived mRNA by cDNA sequencing confirmed the pathogenic character of c.3285-2A>G, which results in an insertion of one nucleotide and a frame shift as the consequence (p.Leu1096IlefsX26)."]), thereby obtaining ACMG evidence criterion was "PS3".

Therefore, inputting any pair (gene name, variant name) or a batch of pairs enabled the obtaining of the corresponding ACMG evidence criterion in a machine automatic literature reading knowledge base constructed based on NLP and knowledge graph technology.

In the NLP-based method for constructing the variant literature interpretation knowledge base according to the embodiments of the present disclosure, the disease-related literature is obtained; then a database of entities associated with genes and variants is constructed based on the disease-related literature; then a literature evidence knowledge graph for interpretation of variant literature can be constructed; and evidence extraction is performed on the literature evidence knowledge graph to obtain evidence corresponding to an entity, and the variant literature interpretation knowledge base can be constructed based on the evidence and the database. In this regard, the present disclosure provides a method for obtaining disease literature evidence by machine automatic literature reading based on NLP and knowledge graph technology. Through the NLP-based method for constructing the variant literature interpretation knowledge base, the literature evidence can be more comprehensive and systematic. the literature evidence can be more comprehensive and systematic. Thus, during interpretation, when any entity name related to gene or variant is input, the result of variant evidence can be automatically returned, thereby achieving the automation and intelligence for obtaining variant literature evidence, and the interpretation speed related to gene and variant can be effectively improved. The literature query result can be returned within seconds, which greatly improves the efficiency of literature search, and is further conducive to improving the quality and efficiency of interpretation of gene detection reports.

Figure 7:
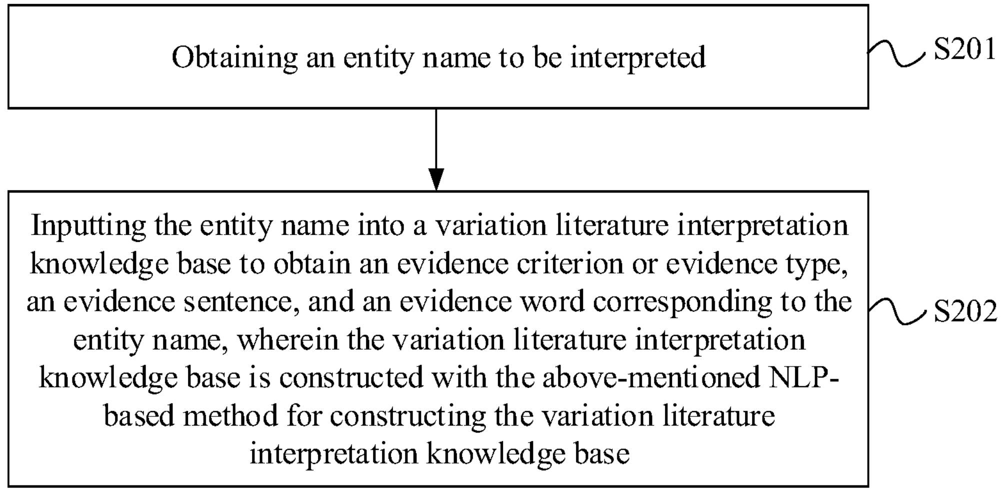
FIG. 7 is a flowchart of an NLP-based variant literature interpretation method according to an embodiment of the present disclosure.

FIG. 7 is a flowchart of an NLP-based variant literature interpretation method according to an embodiment of the present disclosure. Referring to FIG. 7, the NLP-based variant literature interpretation method may include the following steps:

Step S201: the entity name to be interpreted is obtained.

Step S202: the entity name is input into a variant literature interpretation knowledge base to obtain an evidence criterion or evidence type, an evidence sentence, and an evidence word corresponding to the entity name. The variant literature interpretation knowledge base is constructed with the NLP-based method for constructing the variant literature interpretation knowledge base as mentioned above.

For example, the variant literature interpretation knowledge base can be constructed based on the above-mentioned NLP-based method, and a machine automatic literature reading system can be constructed using the variant literature interpretation knowledge base. The system may include a human-computer interaction interface. When a user needs to interpret an entity name, the entity name to be interpreted can be input to the machine automatic literature reading system via the human-computer interaction interface, In this case, the system queries a knowledge base based on the entity name to be interpreted, to obtain evidence criterion or evidence type, the evidence sentence and the evidence word corresponding to the entity name to be interpreted, and returns the results to the interpreter via the human-computer interaction interface.

In the NLP-based variant literature interpretation method according to the embodiment of the present disclosure, the entity name to be interpreted is obtained, and the entity name is input into the variant literature interpretation knowledge base to obtain the evidence criterion or evidence type, the evidence sentence, and the evidence word corresponding to the entity name, in which the variant literature interpretation knowledge base is constructed with the above-mentioned NLP-based method. Thus, the corresponding evidence criteria or evidence types, evidence sentences, and evidence words can be automatically obtained by inputting entity names, thereby achieving the automation and intelligence of obtaining disease variant literature evidence and effectively improving the interpretation speed associated with genes and variants. Thus, the literature evidence is more comprehensive, which is conducive to improving the quality and efficiency of interpretation of gene detection report.

Figure 8:
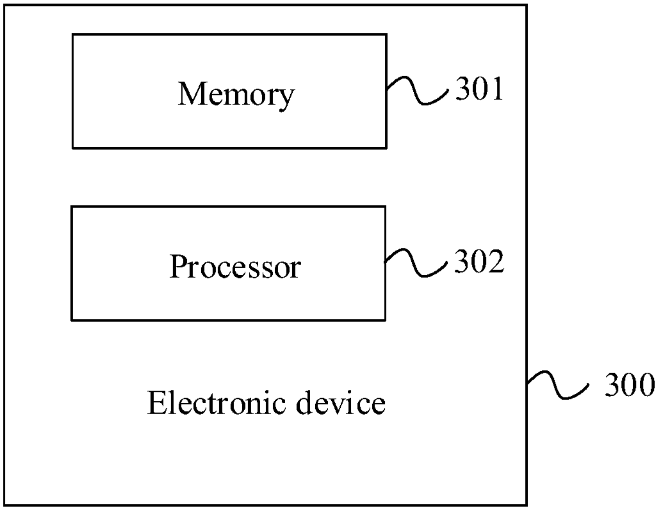
FIG. 8 is a block diagram of the structure of an electronic device according to an embodiment of the present disclosure.

FIG. 8 is a structural block diagram of an electronic device according to an embodiment of the present disclosure. Referring to FIG. 8, the electronic device includes a memory 301, a processor 302, and a variant literature interpretation program stored in the memory 301 and executable on the processor 302. The processor 302, when executing the variant literature interpretation program, implements the NLP-based variant literature interpretation method as described above.

It should be noted that, for the description of the electronic device in the present disclosure, reference is made to the description of the NLP-based variant literature interpretation method in the present disclosure, which will not be repeated herein.

According to the electronic device of the embodiment of the present disclosure, the above-mentioned NLP-based variant literature interpretation method is implemented when the variant literature interpretation program is executed by the processor, such that the corresponding evidence criteria or evidence types, evidence sentences, and evidence words can be automatically obtained by inputting entity names. In this way, the automation and intelligence of obtaining disease variant literature evidence can be achieved, and the interpretation speed associated with genes and variants can be effectively improved. The literature evidence is more comprehensive, which is conducive to improving the quality and efficiency of interpretation of gene detection report.

It should be noted that the logic and/or steps represented in the flowcharts or otherwise described herein can be regarded as an ordered listing of executable instructions for implementing logical functions, and they can be embodied in any computer-readable medium for use by or in connection with an instruction execution system, apparatus, or device, such as a computer-based system, processor-containing system, or other systems that can call the instructions from the instruction execution system, apparatus, or device and execute the instructions.

It should be understood that the respective portions of the present disclosure may be implemented in the form of hardware, software, firmware, or a combination thereof In the embodiments described above, the steps or methods may be implemented in software or firmware stored in memory and executed by a suitable instruction execution system. For example, if they are implemented in the form of hardware, similar as in another embodiment, it may be implemented using any one or combination of the following techniques known in the related art: discrete logic circuits having logic gates for implementing logic functions on data signals, application-specific integrated circuits having appropriate combinational logic gates, programmable gate arrays (PGA), field programmable gate arrays (FPGA), and the like.

In the description of this specification, references to descriptions of the terms “an embodiment”, “some embodiments”, “examples”, “specific examples”, or “some examples”, etc. mean that a particular feature, structure, material, or characteristic described in connection with the embodiment or example is included in at least an embodiment or example of the present disclosure. In this specification, schematic representations of the above terms do not necessarily refer to the same embodiment or example. Furthermore, the particular features, structures, materials, or characteristics described may be combined in any suitable manner in any one or more embodiments or examples.

Furthermore, the terms “first” and “second” are used for descriptive purposes only and are not to be construed as indicating or implying relative importance or implicitly indicating the number of technical features indicated. Thus, a feature defined as “first” or “second” may explicitly or implicitly include at least one such feature. In the description of the present disclosure, the meaning of “plurality” is at least two, e.g., two, three, etc. unless specifically and specifically limited otherwise.

In the present disclosure, unless expressly stated or limited otherwise, the terms “mounted”, “linked”, “connected”, “fixed”, and the like are to be construed broadly, e.g., either fixedly or detachably, or integrally; either a mechanical connection or an electrical connection; either directly connected or indirectly connected through an intermediary, either interconnected between two elements, or in an interactive relationship between two elements, unless explicitly defined otherwise. The specific meaning of the above terms in the present disclosure can be understood by those skilled in the art according to specific circumstances.

While embodiments of the present disclosure have been illustrated and described, it will be understood that the above-described embodiments are illustrative and not restrictive, and that changes, modifications, substitutions, and alterations may be made by those skilled in the art without departing from the scope of the present disclosure.

What is claimed is:

1. A Natural Language Processing (NLP)-based variant literature interpretation method, the method comprising:

constructing a variant literature interpretation knowledge base;

constructing a machine automatic literature reading system using the variant literature interpretation knowledge base, wherein the machine automatic literature reading system comprises a human-computer interaction interface;

obtaining an entity name to be interpreted;

inputting, via the human-computer interaction interface of the machine automatic literature reading system, the entity name into the variant literature interpretation knowledge base to obtain an evidence criterion or evidence type, an evidence sentence, and an evidence word corresponding to the entity name; and returning, via the human-computer interaction interface of the machine automatic literature reading system, the evidence criterion or evidence type, the evidence sentence, and the evidence word corresponding to the entity name to an interpreter, enabling the interpreter to improve the quality and efficiency of interpretation of gene detection report, wherein said constructing the variant literature interpretation knowledge base comprises:

obtaining disease-related literature;

constructing, based on the disease-related literature, a database of entities associated with genes and variants;

constructing a literature evidence knowledge graph for variant interpretation; and performing evidence extraction on the literature evidence knowledge graph to obtain evidence corresponding to an entity, and constructing, based on the evidence and the database, the variant literature interpretation knowledge base, wherein said constructing, based on the disease-related literature, the database of entities associated with genes and variants comprises:

constructing an entity extraction model using some literature of the disease-related literature;

performing, through the entity extraction model, entity extraction on the remaining literature in the disease-related literature to obtain an entity name;

constructing an entity alignment model;

performing, through the entity alignment model, entity alignment on the entity name to obtain an entity standard term corresponding to the entity name; and constructing, based on the entity name and the entity standard term corresponding to the entity name, the database of entities associated with genes and variants.

2. The NLP-based variant literature interpretation method according to claim 1, wherein said constructing the entity extraction model using some literature of the disease-related literature comprises:

performing entity annotating on certain literature;

adding a position and an entity classification tag to each word in the entity-annotated literature to obtain an entity tag sequence;

constructing a pre-training model of the entity extraction model; and adjusting, by using the entity tag sequence, the pre-training model to obtain the entity extraction model.

3. The NLP-based variant literature interpretation method according to claim 2, wherein said constructing the pre-training model of the entity extraction model comprises:

obtaining pre-training corpus, wherein the pre-training corpus comprises relevant literature in the biomedical field;

encoding each word in the pre-training corpus to obtain a word embedding vector, a segment embedding vector, and a position embedding vector;

pre-training, using a back-propagation algorithm, a self-attention mechanism-based NLP model by taking the sum of the word embedding vector, the segment embedding vector, and the position embedding vector as an input and taking a random masking part of a word vector as a tag, to obtain the pre-training model.

4. The NLP-based variant literature interpretation method according to claim 3, wherein said constructing the pre-training model of the entity extraction model further comprises:

training the pre-training model by taking a cross entropy of a predicted value and the tag as a loss function, and not finishing the training of the pre-training model until a loss value output by the loss function satisfies a pre-set condition.

5. The NLP-based variant literature interpretation method according to claim 2, wherein said training, by using the entity tag sequence, the pre-training model to obtain the entity extraction model comprises:

constructing, based on the pre-training model, a fine-tuning model of the entity extraction model; and training, using the back-propagation algorithm, the fine-tuning model to obtain the entity extraction model by taking model weights obtained when training the pre-training model as initial weights of an entity extraction task, taking a word embedding vector corresponding to each word in the entity-annotated literature as an input, and taking the position and the entity classification tag corresponding to each word as an output.

6. The NLP-based variant literature interpretation method according to claim 5, further comprising:

training the fine-tuning model by taking the cross entropy of the predicted value and the tag as the loss function, and not finishing the training of the fine-tuning model until the loss value output by the loss function satisfies the pre-set condition.

7. The NLP-based variant literature interpretation method according to claim 1, further comprising, subsequent to said performing, through the entity extraction model, the entity extraction on the remaining literature in the disease-related literature to obtain the entity name:

matching the remaining literature with a pre-set entity dictionary and/or a pre-set entity writing pattern to supplement an entity name unrecognized by the entity extraction model.

8. The NLP-based variant literature interpretation method according to claim 1, wherein said constructing the entity alignment model comprises:

obtaining an entity standard term and its other entity names, and constructing an entity alignment dictionary based on the entity standard term and the other entity names; and/or obtaining the entity standard term, and constructing an entity-aligned regular expression based on the entity standard term.

9. The NLP-based variant literature interpretation method according to claim 8, wherein the regular expression comprises one or more of the following expressions:

c. {any length number of length≥1 and the number of symbols≥0} {any length letter of length≥1}>{any length letter of length≥1 and the number of symbols≥0};

p. {any length letter of length≥1 and the number of symbols≥0} {any length number of length≥1} {any length letter of length≥1 and the number of symbols≥0};

rs{any length number of length≥1};

chr{any length letter of length≥1}–{any length number of length≥1}–{any length letter of length≥1 and the number of symbols≥0}–{any length letter of length≥1 and the number of symbols≥0};

n. {any length number of length≥1 and the number of symbols≥0} {any length letter of length≥1}>{any length letter of length≥1 and the number of symbols≥0};

IVS. {any length number of length≥1 and the number of symbols≥0} {any length letter of length≥1}>{any length letter of length≥1 and the number of symbols≥0};

{any length letter of length≥1} {any length number of length>1} {any length letter of length≥1}.

10. The NLP-based variant literature interpretation method according to claim 8, wherein said performing, through the entity alignment model, the entity alignment on the entity name to obtain the entity standard term corresponding to the entity name comprises:

performing exact matching and fuzzy matching on the entity name and the entity alignment dictionary to obtain the entity standard term corresponding to the entity name; and/or performing exact matching and rule matching on the entity name and the regular expression to obtain the entity standard term corresponding to the entity name.

11. The NLP-based variant literature interpretation method base according to claim 1, wherein the database of entities associated with genes and variants comprises:

{entity names: entity standard term} dictionary, (literature identification information, entity standard term) data list, and (literature identification information, entity name) data list.

12. The NLP-based variant literature interpretation method according to claim 11, wherein said constructing a literature evidence knowledge graph for interpretation of variant literature comprises:

obtaining a judgment rule of evidence criterion or evidence type used for literature interpretation in variant interpretation guidelines;

presenting the judgment rule in a form of a triplet, wherein the triplet is (entity, relationship between entity and evidence criterion or evidence type, evidence criterion or evidence type); and constructing the literature evidence knowledge graph by taking the entity and the evidence criterion or evidence type as a node and taking a relationship between the entity and the evidence criterion or evidence type as an edge.

13. The NLP-based variant literature interpretation method according to claim 12, wherein said performing the evidence extraction on the literature evidence knowledge graph to obtain the evidence corresponding to the entities, and constructing, based on the evidence and the database, the variant literature interpretation knowledge base comprises:

extracting, from an article corresponding to the database of the entities associated with the genes and variants, a sentence containing the node or a meaning of the node and upper and lower sentences of the sentence, and generating evidence sentence set corresponding to the node;

extracting evidence words representing the relationship from the evidence sentence set;

generating, based on the evidence sentence set and the evidence words, entity standard terms, evidence criteria or evidence types, evidence sentences, and evidence words corresponding to the literature;

constructing the variant literature interpretation knowledge base based on the literature identification information and the entity standard terms, evidence criteria or evidence types, evidence sentences, and evidence words corresponding to the literature.

14. The NLP-based variant literature interpretation method according to claim 1, wherein the entity comprises one or more of a gene, a variant, a drug, a disease, and a phenotype.

15. An electronic device, comprising:

a memory;

a processor; and a variant literature interpretation program stored in the memory and executable on the processor, wherein the processor, when executing the variant literature interpretation program, implements the NLP-based variant literature interpretation method according to claim 1.

* * * * *